(12) United States Patent
Baba

(10) Patent No.: US 11,561,379 B2
(45) Date of Patent: Jan. 24, 2023

(54) OBJECTIVE OPTICAL SYSTEM FOR ENDOSCOPE AND ENDOSCOPE INCLUDING TWO LENS GROUP OF −+ REFRACTIVE POWERS HAVING SIXTH LENSES OF −−+++− REFRACTIVE POWERS

(71) Applicant: FUJIFILM Corporation, Tokyo (JP)

(72) Inventor: Tomoyuki Baba, Saitama (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/723,590

(22) Filed: Apr. 19, 2022

(65) Prior Publication Data

US 2022/0236553 A1    Jul. 28, 2022

Related U.S. Application Data

(63) Continuation of application No. PCT/JP2020/036275, filed on Sep. 25, 2020.

(30) Foreign Application Priority Data

Oct. 24, 2019    (JP) .............................. JP2019-193768

(51) Int. Cl.
*G02B 13/04*    (2006.01)
*A61B 1/00*    (2006.01)
(Continued)

(52) U.S. Cl.
CPC .......... *G02B 13/04* (2013.01); *A61B 1/00163* (2013.01); *G02B 9/10* (2013.01); *G02B 9/62* (2013.01); *G02B 23/243* (2013.01)

(58) Field of Classification Search
CPC . G02B 13/04; G02B 9/10; G02B 9/62; G02B 23/243
See application file for complete search history.

(56) References Cited

U.S. PATENT DOCUMENTS

| | | |
|---|---|---|
| 5,175,650 A | 12/1992 | Takayama et al. |
| 2014/0015999 A1 | 1/2014 | Miyano |

(Continued)

FOREIGN PATENT DOCUMENTS

| | | |
|---|---|---|
| JP | 2596827 B2 | 4/1997 |
| JP | 5635678 B2 | 12/2014 |

(Continued)

OTHER PUBLICATIONS

International Search Report issued in PCT/JP2020/036275; dated Dec. 8, 2020.

(Continued)

*Primary Examiner* — Wen Huang
(74) *Attorney, Agent, or Firm* — Studebaker & Brackett PC

(57) ABSTRACT

An objective optical system for an endoscope consists of, in order from an object side, a negative front group, an aperture stop, and a positive rear group. The front group includes, in order from the object side, only a negative first lens and a cemented lens formed of a negative second lens and a positive third lens cemented to each other, as lenses. The rear group includes, in order from the object side, only a positive fourth lens and a cemented lens formed of a positive fifth lens and a negative sixth lens cemented to each other, as lenses. The objective optical system for an endoscope satisfies predetermined conditional expressions.

14 Claims, 13 Drawing Sheets

(51) Int. Cl.
*G02B 9/62*     (2006.01)
*G02B 23/24*    (2006.01)
*G02B 9/10*     (2006.01)

(56)              References Cited

U.S. PATENT DOCUMENTS

2016/0004064 A1   1/2016   Harada
2016/0178885 A1   6/2016   Harada et al.
2016/0238831 A1   8/2016   Baba
2018/0017777 A1   1/2018   Takasugi
2019/0187454 A1   6/2019   Baba

FOREIGN PATENT DOCUMENTS

JP       2016-014754 A    1/2016
JP       2016-114870 A    6/2016
JP       2016-151629 A    8/2016
JP           6266503 B2   1/2018
JP           6313241 B2   4/2018
JP       2019-109356 A    7/2019
WO       2017/104268 A1   6/2017

OTHER PUBLICATIONS

Written Opinion issued in PCT/JP2020/036275; dated Dec. 8, 2020.
An Office Action; "Notice of Reasons for Refusal," mailed by the Japanese Patent Office dated Oct. 4, 2022, which corresponds to Japanese Patent Application No. 2021-554185 and is related to U.S. Appl. No. 17/723,590; with English language translation.

OBJECTIVE OPTICAL SYSTEM FOR ENDOSCOPE AND ENDOSCOPE INCLUDING TWO LENS GROUP OF −+ REFRACTIVE POWERS HAVING SIXTH LENSES OF −−+++− REFRACTIVE POWERS

CROSS REFERENCE TO RELATED APPLICATIONS

The present application is a Continuation of PCT International Application No. PCT/JP2020/036275, filed on Sep. 25, 2020, which claims priority to Japanese Patent Application No. 2019-193768, filed on Oct. 24, 2019. Each application above is hereby expressly incorporated by reference, in its entirety, into the present application.

BACKGROUND

Technical Field

The present disclosure relates to an objective optical system for an endoscope and an endoscope.

Related Art

In the related art, endoscopes have been used for the observation, treatment, and the like for the inside of a patient's body in a medical field. JP2596827B, JP5635678B, JP6266503B, JP6313241B, and JP2019-109356A disclose lens systems that can be used as an objective optical system for an endoscope.

In recent years, there has been a demand for an objective optical system for an endoscope which has a smaller size and of which various aberrations including a chromatic aberration are satisfactorily corrected.

SUMMARY

The present disclosure provides an objective optical system for an endoscope in which both a reduction in size and the satisfactory correction of various aberrations including a chromatic aberration are achieved and an endoscope comprising the objective optical system for an endoscope.

An objective optical system for an endoscope according to a first aspect of the present disclosure consists of, in order from an object side toward an image side, a front group having negative focal power, an aperture stop, and a rear group having positive focal power. The front group includes only three lenses, which consist of, in order from the object side toward the image side, a first lens having negative focal power, a second lens having negative focal power, and a third lens having positive focal power, as lenses; the rear group includes only three lenses, which consist of, in order from the object side toward the image side, a fourth lens having positive focal power, a fifth lens having positive focal power, and a sixth lens having negative focal power, as lenses; the second lens and the third lens are cemented to each other; the fifth lens and the sixth lens are cemented to each other; and in a case where a focal length of the objective optical system for an endoscope is denoted by f, a focal length of the front group is denoted by fA, a focal length of the rear group is denoted by fB, an Abbe number of the second lens with respect to a d line is denoted by vd2, an Abbe number of the third lens with respect to a d line is denoted by vd3, a refractive index of the second lens with respect to a d line is denoted by Nd2, a refractive index of the third lens with respect to a d line is denoted by Nd3, and a curvature radius of a cemented surface between the second lens and the third lens is denoted by R23, Conditional expressions (1), (2), and (3) are satisfied.

$$-5 < fA/fB < -1.4 \tag{1}$$

$$0 < |vd2-vd3| < 10 \tag{2}$$

$$-6.8 < \{R23/(Nd3-Nd2)\}/f < 0 \tag{3}$$

In the first aspect, it is preferable that at least one of Conditional expression (1-1), (2-1), or (3-1) is satisfied.

$$-2.2 < fA/fB < -1.6 \tag{1-1}$$

$$0.5 < |vd2-vd3| < 5 \tag{2-1}$$

$$-6.4 < \{R23/(Nd3-Nd2)\}/f < -3 \tag{3-1}$$

According to a second aspect of the present disclosure, in the first aspect, it is preferable that a lens surface of the first lens facing the object side is a flat surface.

According to a third aspect of the present disclosure, in the aspect, in a case where a refractive index of the fifth lens with respect to a d line is denoted by Nd5, a refractive index of the sixth lens with respect to a d line is denoted by Nd6, and a curvature radius of a cemented surface between the fifth lens and the sixth lens is denoted by R56, it is preferable that conditional expression (4) is satisfied, and it is more preferable that conditional expression (4-1) is satisfied.

$$-2 < \{R56/(Nd6-Nd5)\}/f < 0 \tag{4}$$

$$-1.9 < \{R56/(Nd5-Nd5)\}/f < -1.4 \tag{4-1}$$

According to a fourth aspect of the present disclosure, in the aspect, in a case where a composite focal length of the second lens and the third lens is denoted by f23 and a composite focal length of the fifth lens and the sixth lens is denoted by f56, it is preferable that conditional expression (5) is satisfied, and it is more preferable that conditional expression (5-1) is satisfied.

$$0 < f23/f56 < 1 \tag{5}$$

$$0.56 < f23/f56 < 0.83 \tag{5-1}$$

According to a fifth aspect of the present disclosure, in the aspect, in a case where a curvature radius of a lens surface of the third lens facing the image side is denoted by R3r, it is preferable that conditional expression (6) is satisfied, and it is more preferable that conditional expression (6-1) is satisfied.

$$-0.45 < (R23+R3r)/(R23-R3r) < -0.25 \tag{6}$$

$$-0.4 < (R23+R3r)/(R23-R3r) < -0.28 \tag{6-1}$$

According to a sixth aspect of the present disclosure, in the aspect, in a case where an Abbe number of the fifth lens with respect to a d line is denoted by vd5 and an Abbe number of the sixth lens with respect to a d line is denoted by vd6, it is preferable that conditional expression (7) is satisfied, and it is more preferable that conditional expression (7-1) is satisfied.

$$35 < |vd5-vd6| < 75 \tag{7}$$

$$38 < |vd5-vd6| < 70 \tag{7-1}$$

An endoscope according to another aspect of the present disclosure comprises the objective optical system for an endoscope according to the aspect of the present disclosure.

"Consisting of" and "consist of" in this specification may intend to include: a lens substantially not having focal power; optical elements other than the lens, such as a stop, a filter, and a cover glass; a lens flange; a lens barrel; and the like in addition to mentioned components.

In this specification, "~ group having positive focal power" means that a group has positive focal power as a whole. Likewise, "~ group having negative focal power" means that a group has negative focal power as a whole. "Single lens" means one lens that is not cemented. However, a complex aspherical lens (that is, a lens in which a spherical lens and an aspherical film formed on the spherical lens are integrated and which functions as one aspherical lens as a whole) is treated as one lens without being regarded as a cemented lens. The sign of focal power, the curvature radius of the lens surface, and the shape of the lens surface of a lens including an aspherical surface are considered in a paraxial region unless otherwise specified. In regard to the sign of a curvature radius, the sign of the curvature radius of a surface having a convex shape toward the object side is positive and the sign of the curvature radius of a surface having a convex shape toward the image side is negative. "The entire system" means "the objective optical system for an endoscope". The "Focal length" used in Conditional expressions is a paraxial focal length. The values of Conditional expressions are values that are obtained in a case where a d line is used as a reference. "d line", "C line", "F line", and "h line" described in this specification are emission lines, and the wavelength of a d line is 587.56 nm (nanometer), the wavelength of a C line is 656.27 nm (nanometer), the wavelength of an F line is 486.13 nm (nanometer), and the wavelength of an h line is 404.66 nm (nanometer).

According to the aspects, the objective optical system for an endoscope of the present disclosure and the endoscope comprising the objective optical system for an endoscope can achieve both a reduction in size and the satisfactory correction of various aberrations including a chromatic aberration.

DETAILED DESCRIPTION

Figure 1:
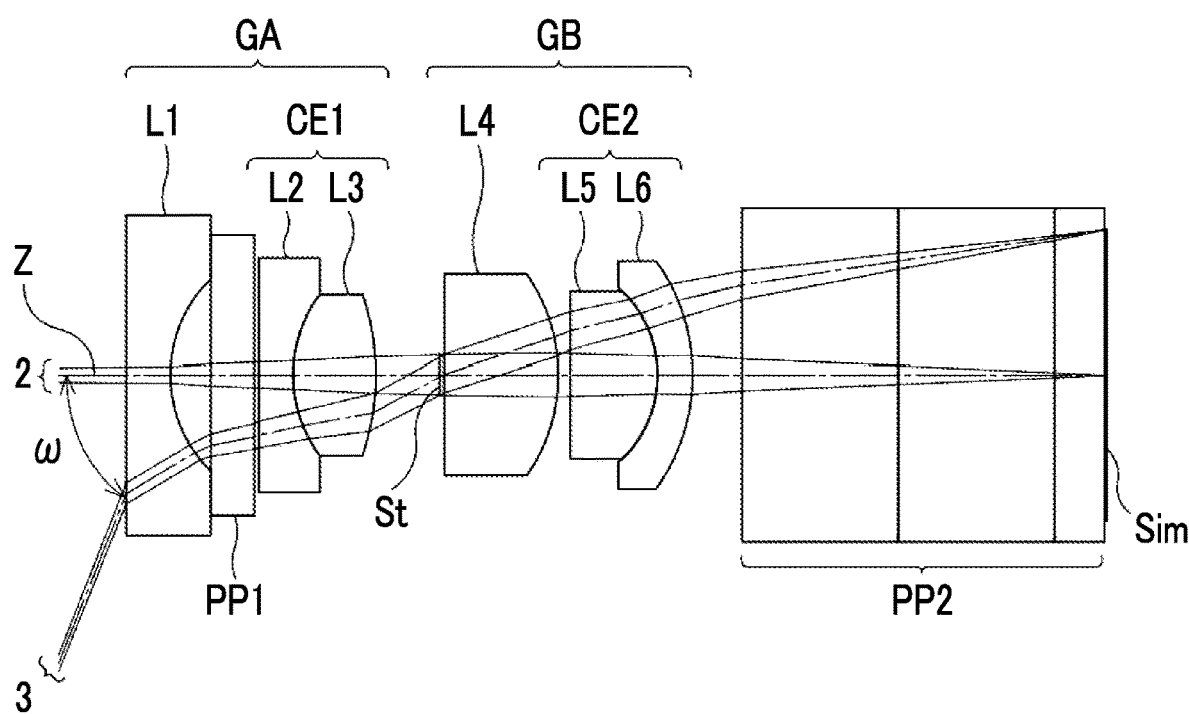
FIG. 1 is a cross-sectional view showing the configuration and optical paths of an objective optical system for an endoscope according to an exemplary embodiment (an objective optical system for an endoscope of Example 1).

Exemplary embodiments of the present disclosure will be described in detail below with reference to the drawings. FIG. 1 is a diagram showing the configuration and optical paths of an objective optical system for an endoscope according to an exemplary embodiment of the present disclosure on a cross section including an optical axis Z, and corresponds to the lens configuration of Example 1 to be described later. In FIG. 1, a left side is an object side, a right side is an image side, the optical paths mean the optical path of on-axis luminous flux 2 and the optical path of luminous flux 3 with the maximum angle of view, and the half angle ω of view of the principal ray of the luminous flux 3 is also shown. ω shown in FIG. 1 corresponds to the half value of the maximum total angle of view.

The objective optical system for an endoscope according to this exemplary embodiment consists of a front group GA having negative focal power, an aperture stop St, and a rear group GB having positive focal power that are arranged along the optical axis Z in order from the object side toward the image side. Since the negative lens group and the positive lens group are arranged in this order from the object side, a retrofocus type lens system is formed. Accordingly, an optical system, which can ensure a back focus and suitably cope with a wide angle of view required for an endoscope, is formed. The aperture stop St shown in FIG. 1 does not necessarily represent a size or a shape and represents the position thereof on the optical axis Z.

The front group GA comprises only three lenses, which consist of, in order from the object side toward the image side, a first lens L1 having negative focal power, a second lens L2 having negative focal power, and a third lens L3 having positive focal power, as lenses. The first lens L1 is a single lens. The second lens L2 and the third lens L3 are cemented to each other and form a first cemented lens CE1. Distortion and field curvature can be suppressed by the first lens L1. Since an axial chromatic aberration and a lateral chromatic aberration can be suppressed by the first cemented lens CE1, it is advantageous in suppressing an axial chromatic aberration and a lateral chromatic aberration over the entire range to a visible range from a short wavelength range near a wavelength of 400 nm (nanometer).

It is preferable that the lens surface of the first lens L1 facing the object side is a flat surface, and the outer diameter of the first lens L1 can be reduced in this case. Further, in a case where the lens surface of the first lens L1 facing the object side is formed of a flat surface, manufacturability can be improved and the adhesion of dust, liquid, and/or the like to the surface of the first lens L1 facing the object side can be reduced.

In the example shown in FIG. 1, an optical member PP1 is disposed between the first lens L1 and the second lens L2. The optical member PP1 is a member of which the incident surface and the emission surface are parallel to each other and which does not have focal power, and is not a lens. The optical member PP1 may be omitted in this exemplary embodiment. The optical member PP1 may be adapted to have a filter function as necessary.

The rear group GB comprises only three lenses, which consist of, in order from the object side toward the image side, a fourth lens L4 having positive focal power, a fifth lens L5 having positive focal power, and a sixth lens L6 having negative focal power, as lenses. The fourth lens L4 is a single lens. The fifth lens L5 and the sixth lens L6 are cemented to each other and form a second cemented lens CE2. A spherical aberration can be suppressed by the fourth lens L4. Since a lateral chromatic aberration can be suppressed by the second cemented lens CE2, it is advantageous in suppressing a lateral chromatic aberration over the entire range to a visible range from a short wavelength range near a wavelength of 400 nm (nanometer).

In the example shown in FIG. 1, an optical member PP2 is disposed between the sixth lens L6 and an image plane Sim. The optical member PP2 is a member of which the incident surface and the emission surface are parallel to each other and which does not have focal power, and is not a lens. A prism, a filter, a cover glass, and/or the like are assumed as the optical member PP2. In a case where a prism for bending an optical path is used as the optical member PP2, optical paths become bent optical paths but a diagram in which optical paths are developed is shown in FIG. 1 for easy understanding. The optical member PP2 may be omitted in this exemplary embodiment.

The objective optical system for an endoscope according to this exemplary embodiment satisfies the following conditional expression (1) in a case where the focal length of the front group GA is denoted by fA and the focal length of the rear group GB is denoted by fB. In a case where fA/fB is made to be larger than the lower limit of Conditional expression (1), the outer diameter of the lens system can be reduced. In a case where fA/fB is made to be smaller than the upper limit of Conditional expression (1), it is advantageous in increasing the angle of view. In addition, in a case where the objective optical system for an endoscope according to this exemplary embodiment is adapted to satisfy the following conditional expression (1-1), better characteristics can be obtained.

$$-5 < fA/fB < -1.4 \qquad (1),$$

$$-2.2 < fA/fB < -1.6 \qquad (1\text{-}1)$$

Further, the objective optical system for an endoscope according to this exemplary embodiment satisfies the following conditional expression (2) in a case where the Abbe number of the second lens L2 with respect to a d line is denoted by vd2 and the Abbe number of the third lens L3 with respect to a d line is denoted by vd3. In a case where |vd2−vd3| is made to be larger than the lower limit of Conditional expression (2), it is advantageous in suppressing an axial chromatic aberration and a lateral chromatic aberration over the entire range to a visible range from a short wavelength range near a wavelength of 400 nm (nanometer). Since it is possible to suppress the excess of the correction amounts of an axial chromatic aberration and a lateral chromatic aberration in a case where |vd2−vd3| is made to be smaller than the upper limit of Conditional expression (2), it is possible to suitably control an axial chromatic aberration and a lateral chromatic aberration. Furthermore, in a case where the objective optical system for an endoscope according to this exemplary embodiment is adapted to satisfy the following conditional expression (2-1), better characteristics can be obtained.

$$0 < |vd2-vd3| < 10 \qquad (2)$$

$$0.5 < |vd2-vd3| < 5 \qquad (2\text{-}1)$$

Further, the objective optical system for an endoscope according to this exemplary embodiment satisfies the following conditional expression (3) in a case where the focal length of the entire system is denoted by f, the refractive index of the second lens L2 with respect to a d line is denoted by Nd2, the refractive index of the third lens L3 with respect to a d line is denoted by Nd3, and the curvature radius of a cemented surface between the second lens L2 and the third lens L3 is denoted by R23. In a case where {R23/(Nd3−Nd2)} is made to be larger than the lower limit of Conditional expression (3), the outer diameter of the lens system can be reduced while an axial chromatic aberration and a lateral chromatic aberration are suitably controlled. In a case where {R23/(Nd3−Nd2)} is made to be smaller than the upper limit of Conditional expression (3), it is advantageous in increasing the angle of view while suitably controlling an axial chromatic aberration and a lateral chromatic aberration. Furthermore, in a case where the objective optical system for an endoscope according to this exemplary embodiment is adapted to satisfy the following conditional expression (3-1), better characteristics can be obtained.

$$-6.8 < \{R23/(Nd3-Nd2)\}/f < 0 \qquad (3).$$

$$-6.4 < \{R23/(Nd3-Nd2)\}/f < -3 \qquad (3\text{-}1).$$

In addition, it is preferable that the objective optical system for an endoscope according to this exemplary embodiment satisfies the following conditional expression (4) in a case where the refractive index of the fifth lens L5 with respect to a d line is denoted by Nd5, the refractive index of the sixth lens L6 with respect to a d line is denoted by Nd6, and the curvature radius of a cemented surface between the fifth lens L5 and the sixth lens L6 is denoted by R56. In a case where {R56/(Nd6−Nd5)} is made to be in the range of Conditional expression (4), it is possible to satisfactorily suppress field curvature while suitably controlling an axial chromatic aberration and a lateral chromatic aberration. Moreover, in a case where the objective optical system for an endoscope according to this exemplary embodiment is adapted to satisfy the following conditional expression (4-1), better characteristics can be obtained.

$$-2 < \{R56/(Nd6-Nd5)\}/f < 0 \qquad (4)$$

$$-1.9 < \{R56/(Nd6-Nd5)\}/f < -1.4 \qquad (4\text{-}1)$$

Further, it is preferable that the objective optical system for an endoscope according to this exemplary embodiment satisfies the following conditional expression (5) in a case where the composite focal length of the second lens L2 and the third lens L3 is denoted by f23 and the composite focal length of the fifth lens L5 and the sixth lens L6 is denoted by f56. In a case where f23/f56 is made to be in the range of Conditional expression (5), it is possible to satisfactorily suppress a spherical aberration and field curvature. Furthermore, in a case where the objective optical system for an endoscope according to this exemplary embodiment is adapted to satisfy the following conditional expression (5-1), better characteristics can be obtained.

$$0 < f23/f56 < 1 \qquad (5)$$

$$0.56 < f23/f56 < 0.83 \qquad (5\text{-}1)$$

Further, it is preferable that the objective optical system for an endoscope according to this exemplary embodiment satisfies the following conditional expression (6) in a case where the curvature radius of the lens surface of the third lens L3 facing the image side is denoted by R3r. In a case where (R23+R3r)/(R23−R3r) is made to be in the range of Conditional expression (6), it is possible to satisfactorily suppress a spherical aberration and field curvature. Furthermore, in a case where the objective optical system for an endoscope according to this exemplary embodiment is adapted to satisfy the following conditional expression (6-1), better characteristics can be obtained.

$$-0.45 < (R23+R3r)/(R23-R3r) < -0.25 \quad (6)$$

$$-0.4 < (R23+R3r)/(R23-R3r) < -0.28 \quad (6\text{-}1)$$

Further, it is preferable that the objective optical system for an endoscope according to this exemplary embodiment satisfies the following conditional expression (7) in a case where the Abbe number of the fifth lens L5 with respect to a d line is denoted by vd5 and the Abbe number of the sixth lens L6 with respect to a d line is denoted by vd6. In a case where |vd5−vd6| is made to be larger than the lower limit of Conditional expression (7), it is advantageous in suppressing an axial chromatic aberration and a lateral chromatic aberration over the entire range to a visible range from a short wavelength range near a wavelength of 400 nm (nanometer). Since it is possible to suppress the excess of the correction amounts of an axial chromatic aberration and a lateral chromatic aberration in a case where |vd5−vd6| is made to be smaller than the upper limit of Conditional expression (7), it is possible to suitably control an axial chromatic aberration and a lateral chromatic aberration. Furthermore, in a case where the objective optical system for an endoscope according to this exemplary embodiment is adapted to satisfy the following conditional expression (7-1), better characteristics can be obtained.

$$35 < |vd5-vd6| < 75 \quad (7)$$

$$38 < |vd5-vd6| < 70 \quad (7\text{-}1)$$

Since the above-mentioned preferred configurations and possible configurations can be randomly combined, it is preferable that the above-mentioned preferred configurations and possible configurations are appropriately selectively employed according to specifications to be required.

Next, numerical examples of the objective optical system for an endoscope according to the exemplary embodiment of the present disclosure will be described. Basic lens data of Examples 1 to 6 to be described below and diagrams showing aberrations are obtained in consideration of a state in which an endoscope is used in a case where an object (not shown) having a certain curvature at a finite distance is observed. Reference numerals given to the lenses in cross-sectional views of the respective examples are used independently for every example in order to avoid the complication of description caused by an increase in the number of digits of the reference numerals. Accordingly, even though common reference numerals are given to components in the drawings of different examples, the components are not necessarily common.

Example 1

Since a cross-sectional view showing the configuration and optical paths of an objective optical system for an endoscope of Example 1 is shown in FIG. 1 and a showing method thereof is the same as described above, the repeated description thereof will be partially omitted here. The basic lens data of the objective optical system for an endoscope of Example 1 are shown in Table 1, and specifications thereof are shown in Table 2. In Table 1, surface numbers, which are obtained in a case where a surface closest to the object side is set as a first surface and a number is increased toward the image side one by one, are shown in the column of Sn, the curvature radii of the respective surfaces are shown in the column of R, and a surface spacing on the optical axis between each surface and a surface adjacent to the image side thereof is shown in the column of D. Further, the refractive indexes of the respective components with respect to a d line are shown in the column of Nd, and the Abbe numbers of the respective components with respect to a d line are shown in the column of vd.

In Table 1, the sign of the curvature radius of a surface having a convex shape toward the object side is set to be positive and the sign of the curvature radius of a surface having a convex shape toward the image side is set to be negative. An object, the aperture stop St, the optical member PP1, and the optical member PP2 are also shown in Table 1 together. In Table 1, OBJ is written in the space of the surface number of a surface corresponding to the object and the surface number and the expression of (St) are written in the space of the surface number of a surface corresponding to the aperture stop St. A value written in the lowest space of the column of D in Table 1 is a spacing between a surface, which is closest to the image side in Table 1, and the image plane Sim.

The value of the focal length f of the entire system and the values of the back focus Bf, the F-Number FNo., and the maximum total angle 2ω of view of the entire system at an air conversion distance are shown in Table 2 with respect to a d line. (°) shown in the space of 2ω means that a unit is a degree.

A degree is used as the unit of an angle and mm (millimeter) is used as the unit of a length in the data of the respective Tables, but other appropriate units can also be used since an optical system can be used even in the case of a proportional increase in size or a proportional reduction in size. Further, numerical values, which are rounded off to a predetermined place, are written in each Table to be described below.

TABLE 1

Example 1

| Sn | R | D | Nd | vd |
|---|---|---|---|---|
| OBJ | 6.9500 | 6.9500 | | |
| 1 | ∞ | 0.3500 | 1.88299 | 40.78 |
| 2 | 0.9530 | 0.3200 | | |
| 3 | ∞ | 0.3500 | 2.00069 | 25.46 |
| 4 | ∞ | 0.0350 | | |
| 5 | ∞ | 0.2800 | 1.95375 | 32.32 |
| 6 | 0.9530 | 0.6600 | 1.78880 | 28.43 |
| 7 | −1.7420 | 0.5275 | | |
| 8 (St) | ∞ | 0.0175 | | |
| 9 | ∞ | 0.9100 | 1.49700 | 81.54 |
| 10 | −1.2500 | 0.1000 | | |
| 11 | ∞ | 0.6900 | 1.49700 | 81.54 |
| 12 | −0.8320 | 0.2800 | 2.00069 | 25.46 |
| 13 | −1.3820 | 0.3961 | | |
| 14 | ∞ | 1.2500 | 1.55919 | 53.90 |
| 15 | ∞ | 1.2500 | 1.55919 | 53.90 |
| 16 | ∞ | 0.4000 | 1.47144 | 65.41 |
| 17 | ∞ | 0.0153 | | |

TABLE 2

| Example 1 | |
|---|---|
| f | 1.033 |
| Bf | 2.145 |
| FNo. | 7.93 |
| 2ω (°) | 134.0 |

Figure 2:
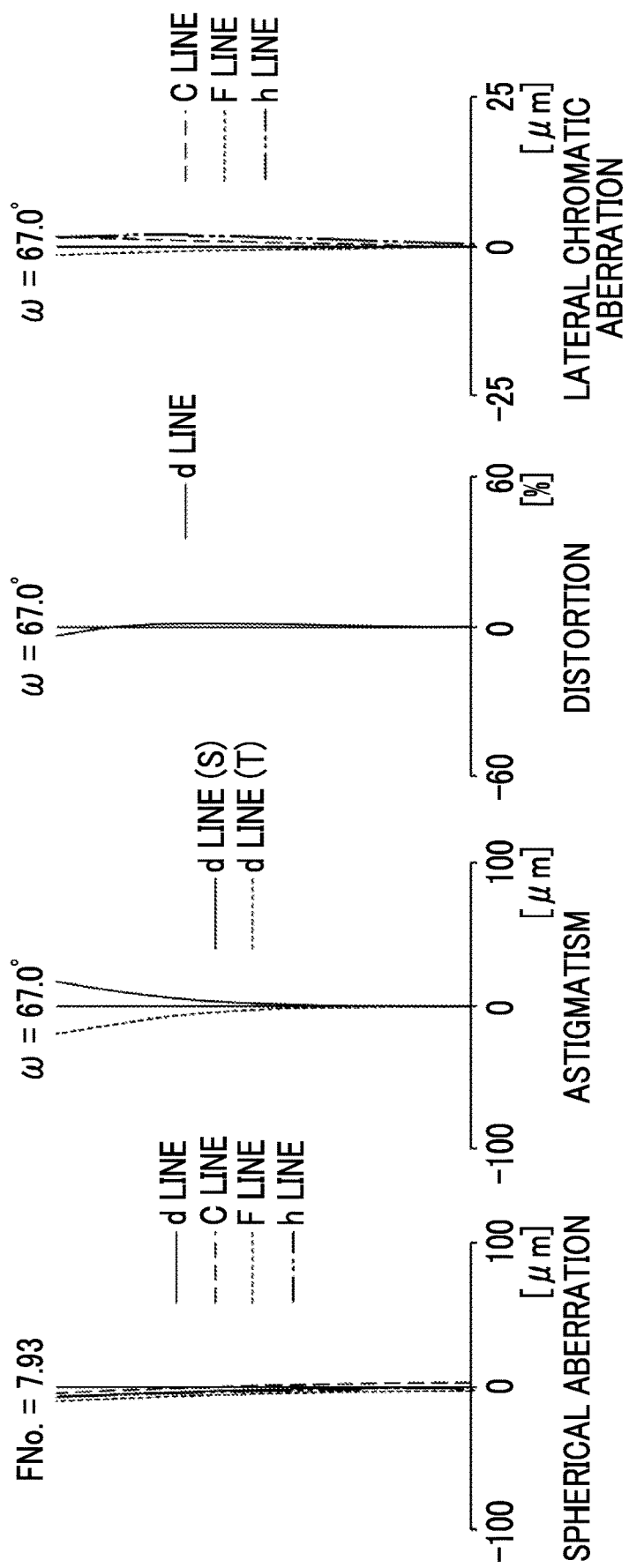
FIG. 2 is a diagram showing the respective aberrations of the objective optical system for an endoscope of Example 1.

A diagram showing the respective aberrations of the objective optical system for an endoscope of Example 1 is shown in FIG. 2. A spherical aberration, astigmatism, distortion, and a lateral chromatic aberration are shown in FIG. 2 in this order from the left. In the diagram showing the spherical aberration, aberrations with respect to a d line, a C line, an F line, and an h line are shown by a black solid line, a black long-dashed line, a black short-dashed line, and a black two-dot chain line, respectively. In the diagram showing the astigmatism, an aberration in a sagittal direction with respect to a d line is shown by a solid line and an aberration in a tangential direction with respect to a d line is shown by a short-dashed line. In the diagram showing the distortion, an aberration with respect to a d line is shown by a solid line. In the diagram showing the lateral chromatic aberration, aberrations with respect to a C line, an F line, and an h line are shown by a long-dashed line, a short-dashed line, and a two-dot chain line, respectively. FNo. in the diagram showing the spherical aberration means an F-Number and ω in the diagrams showing the other aberrations means the half angle of view.

Since the symbols, meanings, writing methods, showing methods for data about Example 1 are the same as those of other examples to be described below unless otherwise specified, the repeated description thereof will be omitted below.

Example 2

Figure 3:
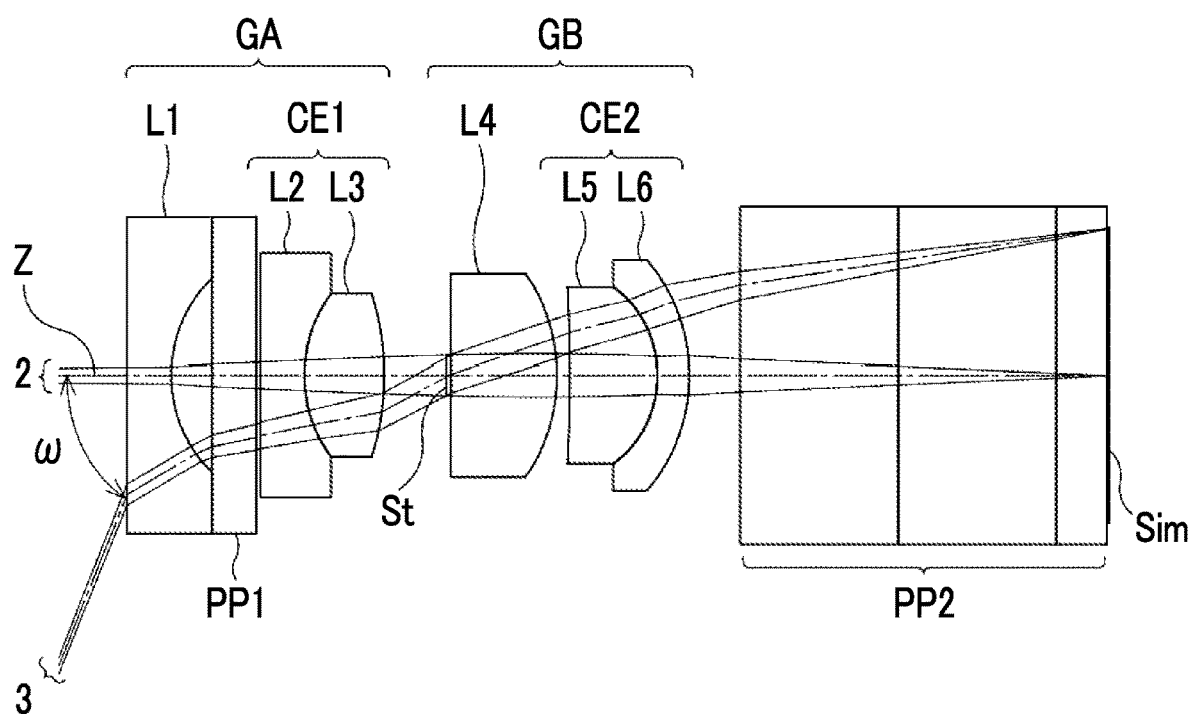
FIG. 3 is a cross-sectional view showing the configuration and optical paths of an objective optical system for an endoscope of Example 2.
Figure 4:
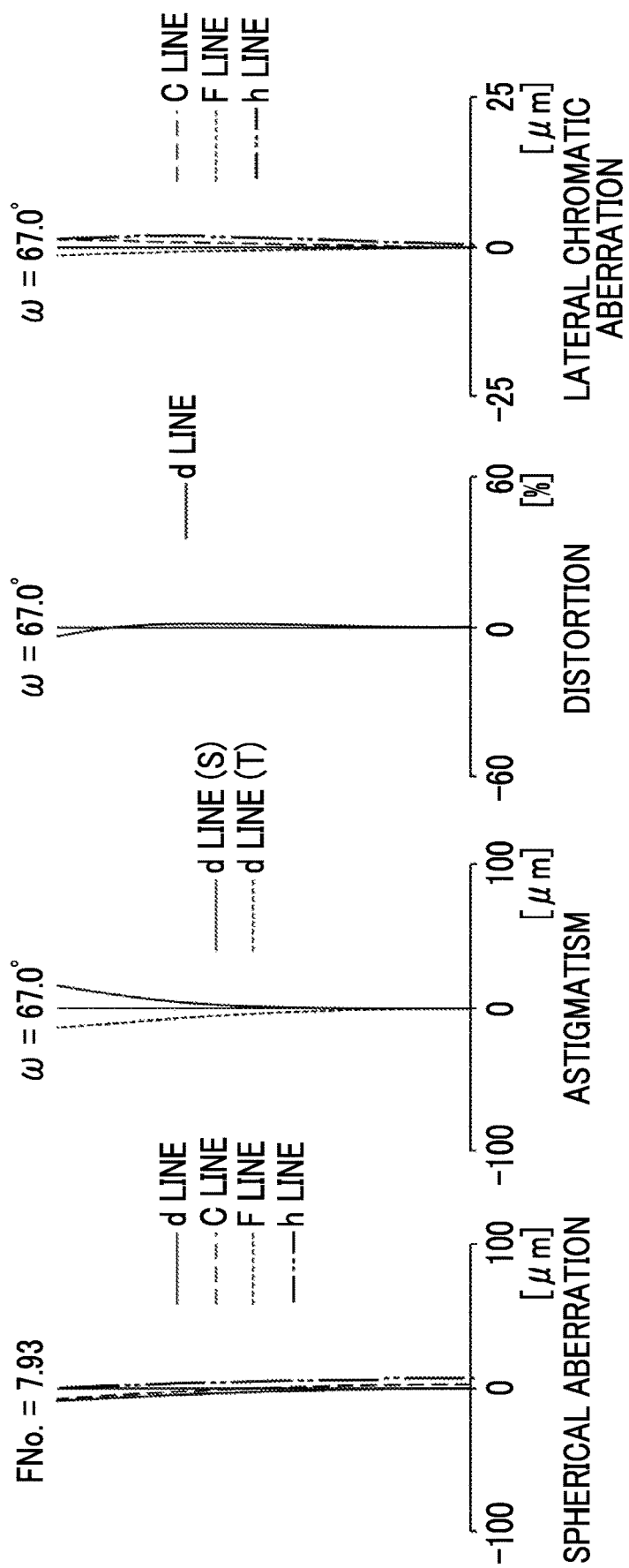
FIG. 4 is a diagram showing the respective aberrations of the objective optical system for an endoscope of Example 2.

A cross-sectional view showing the configuration and optical paths of an objective optical system for an endoscope of Example 2 is shown in FIG. 3, the basic lens data thereof are shown in Table 3, the specifications thereof are shown in Table 4, and a diagram showing the respective aberrations thereof is shown in FIG. 4.

TABLE 3

| Example 2 | | | | |
|---|---|---|---|---|
| Sn | R | D | Nd | vd |
| OBJ | 7.1000 | 7.1000 | | |
| 1 | ∞ | 0.3500 | 1.88299 | 40.78 |
| 2 | 0.9530 | 0.3200 | | |
| 3 | ∞ | 0.3500 | 1.95906 | 17.47 |
| 4 | ∞ | 0.0350 | | |
| 5 | ∞ | 0.3500 | 2.00069 | 25.46 |
| 6 | 0.9530 | 0.6300 | 1.85478 | 24.80 |
| 7 | −1.9010 | 0.5075 | | |
| 8 (St) | ∞ | 0.0175 | | |
| 9 | ∞ | 0.8400 | 1.49700 | 81.54 |
| 10 | −1.2500 | 0.1000 | | |
| 11 | −13.5880 | 0.6900 | 1.49700 | 81.54 |
| 12 | −0.7780 | 0.2500 | 2.00069 | 25.46 |
| 13 | −1.2500 | 0.4044 | | |
| 14 | ∞ | 1.2500 | 1.55919 | 53.90 |
| 15 | ∞ | 1.2500 | 1.55919 | 53.90 |
| 16 | ∞ | 0.4000 | 1.47144 | 65.41 |
| 17 | ∞ | 0.0161 | | |

TABLE 4

| Example 2 | |
|---|---|
| f | 1.035 |
| Bf | 2.156 |
| FNo. | 7.93 |
| 2ω (°) | 134.0 |

Example 3

Figure 5:
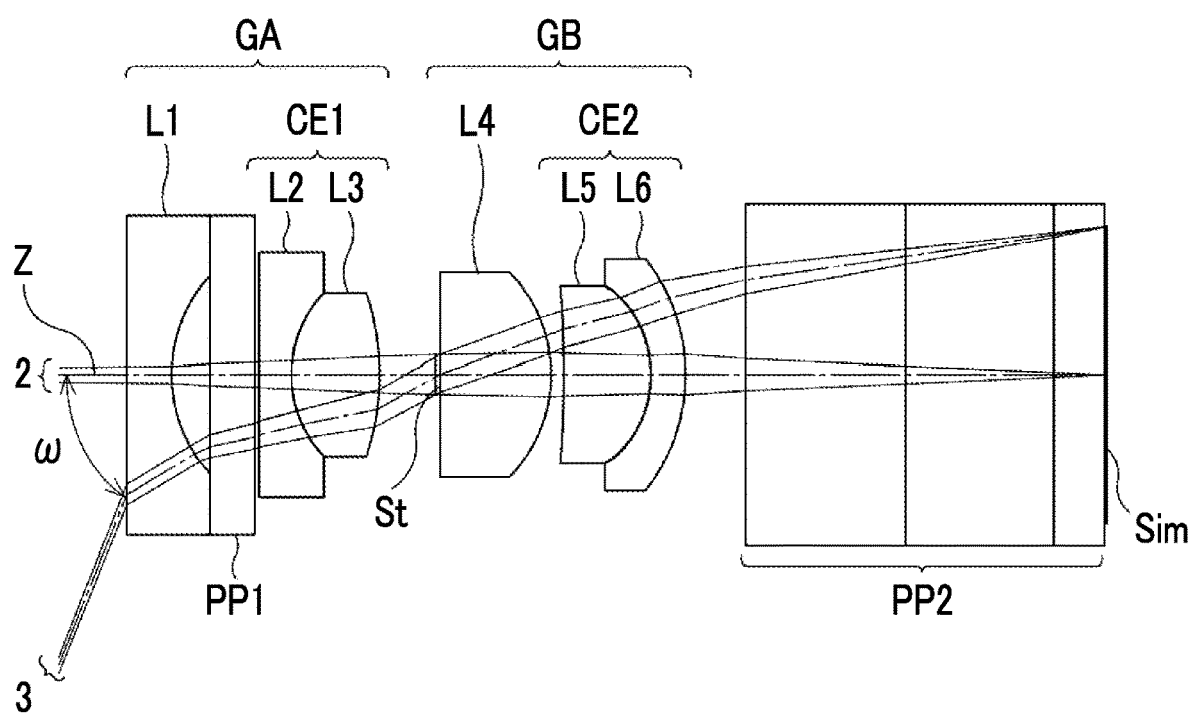
FIG. 5 is a cross-sectional view showing the configuration and optical paths of an objective optical system for an endoscope of Example 3.
Figure 6:
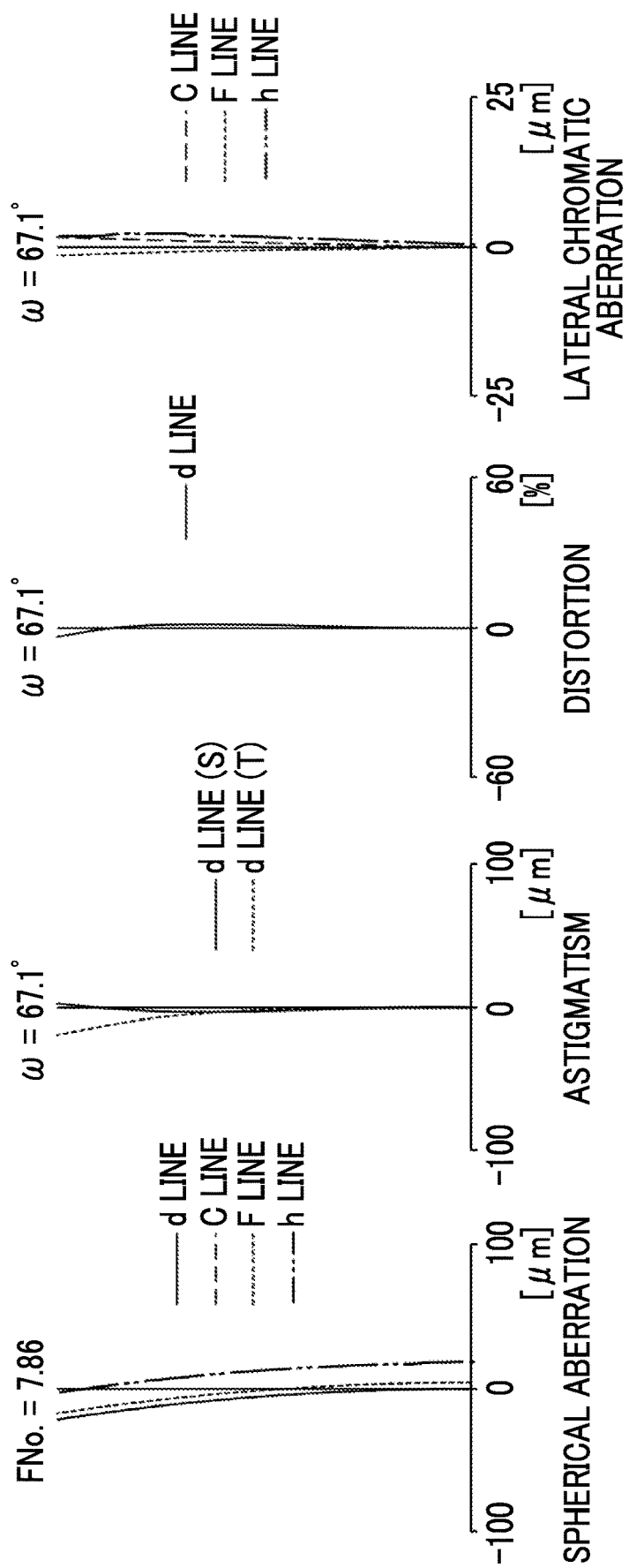
FIG. 6 is a diagram showing the respective aberrations of the objective optical system for an endoscope of Example 3.

A cross-sectional view showing the configuration and optical paths of an objective optical system for an endoscope of Example 3 is shown in FIG. 5, the basic lens data thereof are shown in Table 5, the specifications thereof are shown in Table 6, and a diagram showing the respective aberrations thereof is shown in FIG. 6.

TABLE 5

| Example 3 | | | | |
|---|---|---|---|---|
| Sn | R | D | Nd | vd |
| OBJ | 7.1000 | 7.1000 | | |
| 1 | ∞ | 0.3500 | 1.88299 | 40.78 |
| 2 | 1.0220 | 0.3000 | | |
| 3 | ∞ | 0.3500 | 2.00100 | 29.13 |
| 4 | ∞ | 0.0350 | | |
| 5 | ∞ | 0.2600 | 1.95375 | 32.32 |
| 6 | 0.8320 | 0.6900 | 1.78880 | 28.43 |
| 7 | −1.8180 | 0.4400 | | |
| 8 (St) | ∞ | 0.0350 | | |
| 9 | ∞ | 0.8700 | 1.43875 | 94.66 |
| 10 | −1.0220 | 0.1000 | | |
| 11 | −8.3060 | 0.6800 | 1.53775 | 74.70 |
| 12 | −0.7780 | 0.2700 | 2.00069 | 25.46 |
| 13 | −1.3040 | 0.4720 | | |
| 14 | ∞ | 1.2600 | 1.55919 | 53.90 |
| 15 | ∞ | 1.1600 | 1.55919 | 53.90 |
| 16 | ∞ | 0.4000 | 1.47144 | 65.41 |
| 17 | ∞ | 0.0158 | | |

TABLE 6

| Example 3 | |
|---|---|
| f | 1.032 |
| Bf | 2.174 |
| FNo. | 7.86 |
| 2ω (°) | 134.2 |

Example 4

Figure 7:
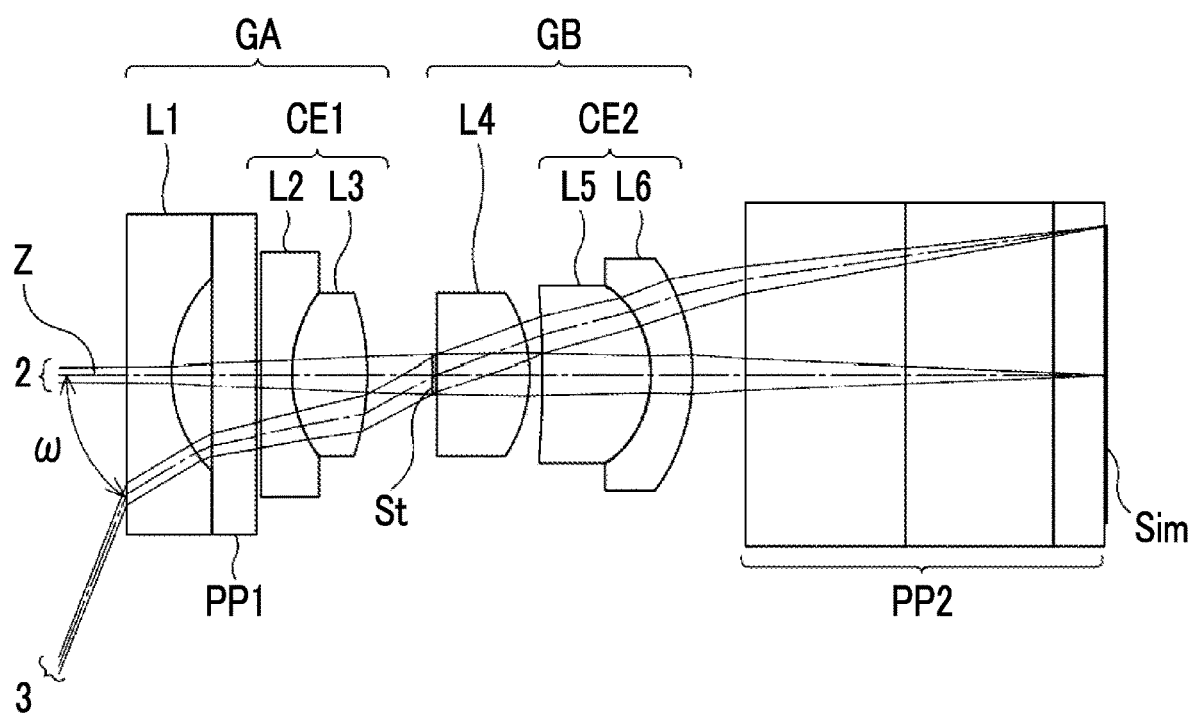
FIG. 7 is a cross-sectional view showing the configuration and optical paths of an objective optical system for an endoscope of Example 4.
Figure 8:
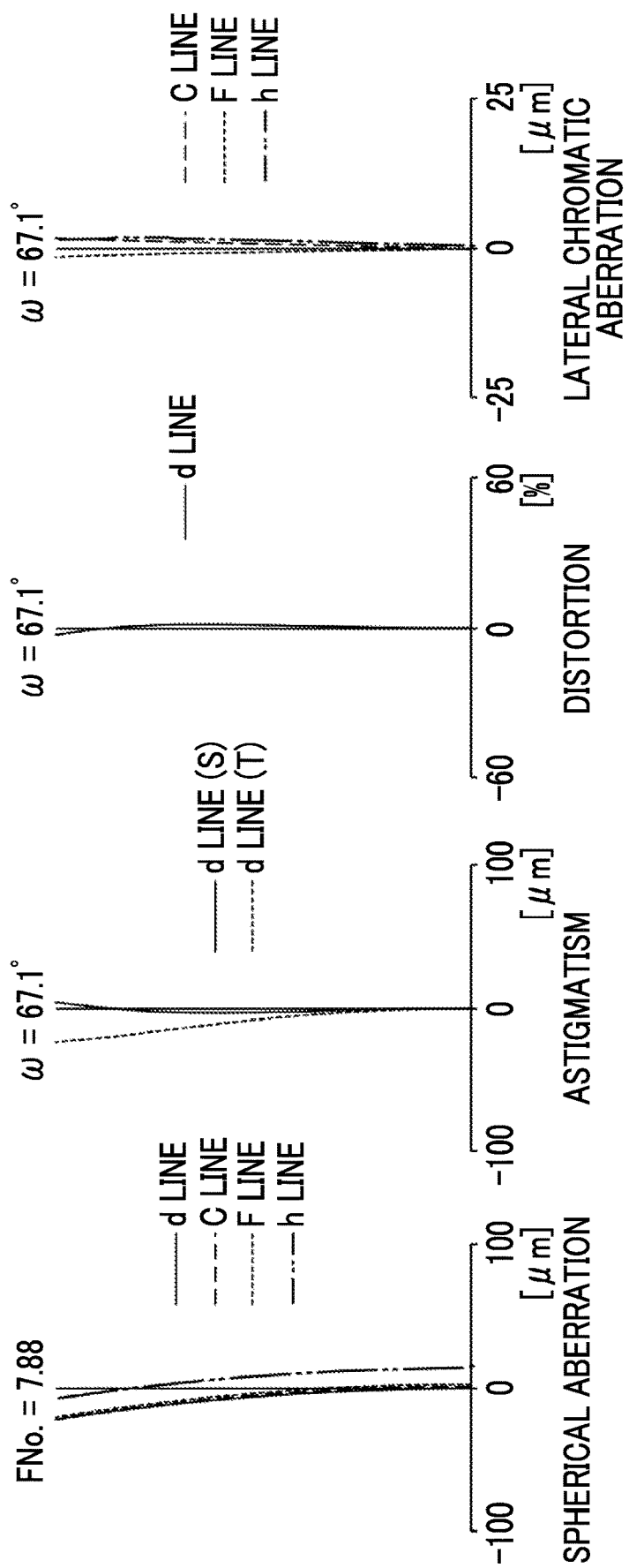
FIG. 8 is a diagram showing the respective aberrations of the objective optical system for an endoscope of Example 4.

A cross-sectional view showing the configuration and optical paths of an objective optical system for an endoscope of Example 4 is shown in FIG. 7, the basic lens data thereof are shown in Table 7, the specifications thereof are shown in Table 8, and a diagram showing the respective aberrations thereof is shown in FIG. 8.

TABLE 7

| Example 4 | | | | |
|---|---|---|---|---|
| Sn | R | D | Nd | vd |
| OBJ | 7.1000 | 7.1000 | | |
| 1 | ∞ | 0.3500 | 1.88299 | 40.78 |
| 2 | 0.9530 | 0.3141 | | |
| 3 | ∞ | 0.3500 | 2.00100 | 29.13 |

TABLE 7-continued

Example 4

| Sn | R | D | Nd | vd |
|---|---|---|---|---|
| 4 | ∞ | 0.0350 | | |
| 5 | ∞ | 0.2490 | 1.95375 | 32.32 |
| 6 | 0.9530 | 0.5908 | 1.78880 | 28.43 |
| 7 | −1.7420 | 0.5102 | | |
| 8 (St) | ∞ | 0.0350 | | |
| 9 | ∞ | 0.7288 | 1.43875 | 94.66 |
| 10 | −1.0220 | 0.0992 | | |
| 11 | −7.1980 | 0.8492 | 1.59522 | 67.73 |
| 12 | −0.7780 | 0.3243 | 2.00069 | 25.46 |
| 13 | −1.3820 | 0.4144 | | |
| 14 | ∞ | 1.2600 | 1.55919 | 53.90 |
| 15 | ∞ | 1.1600 | 1.55919 | 53.90 |
| 16 | ∞ | 0.4000 | 1.47144 | 65.41 |
| 17 | ∞ | 0.0177 | | |

TABLE 8

Example 4

| | |
|---|---|
| f | 1.029 |
| Bf | 2.118 |
| FNo. | 7.88 |
| 2ω (°) | 134.2 |

Example 5

Figure 9:
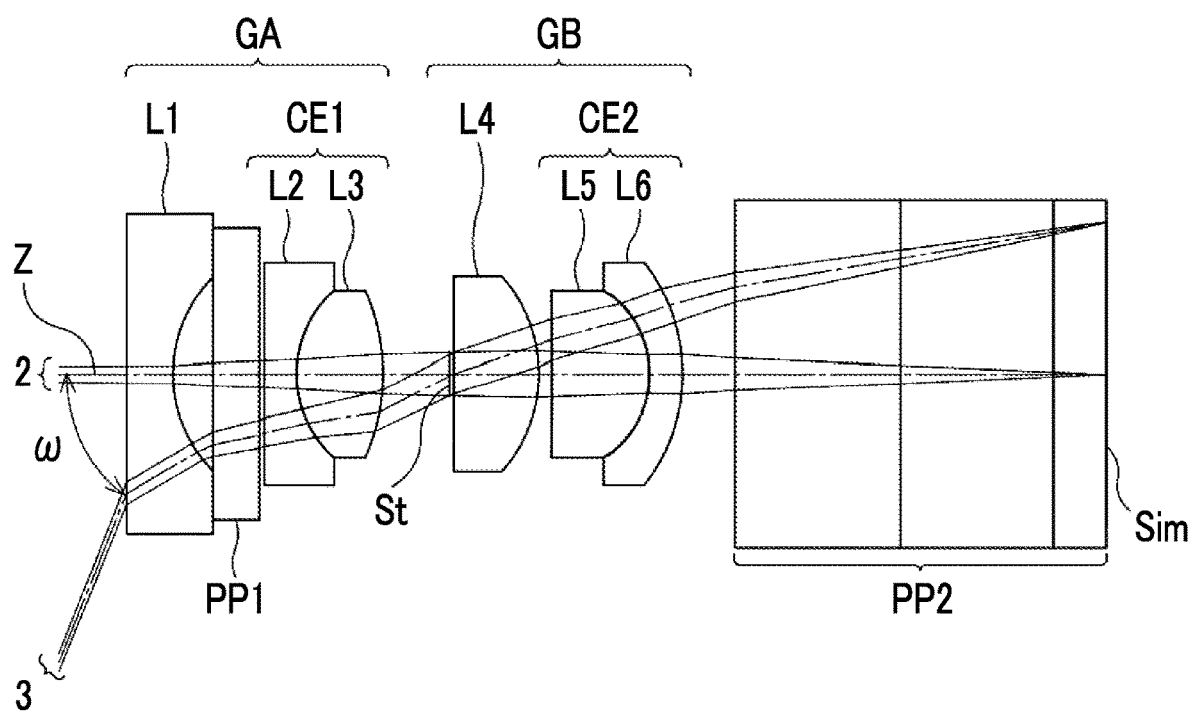
FIG. 9 is a cross-sectional view showing the configuration and optical paths of an objective optical system for an endoscope of Example 5.
Figure 10:
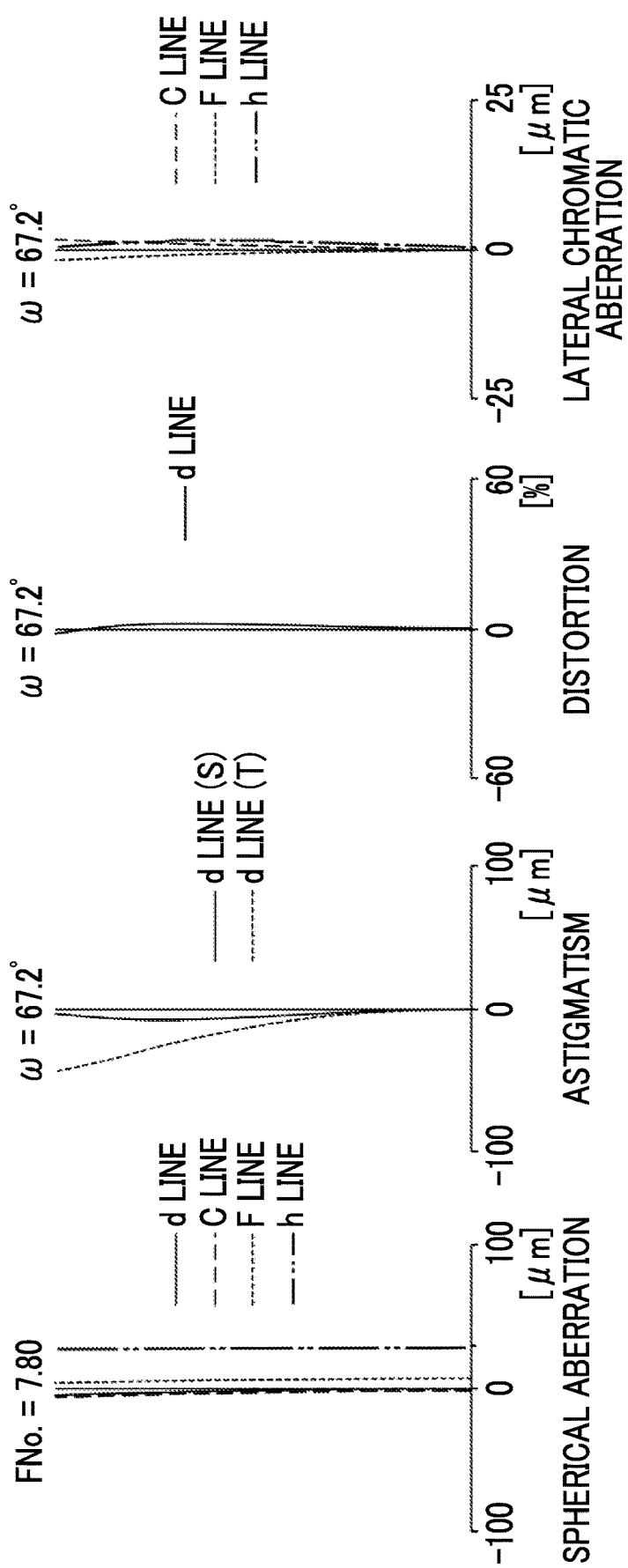
FIG. 10 is a diagram showing the respective aberrations of the objective optical system for an endoscope of Example 5.

A cross-sectional view showing the configuration and optical paths of an objective optical system for an endoscope of Example 5 is shown in FIG. 9, the basic lens data thereof are shown in Table 9, the specifications thereof are shown in Table 10, and a diagram showing the respective aberrations thereof is shown in FIG. 10.

TABLE 9

Example 5

| Sn | R | D | Nd | vd |
|---|---|---|---|---|
| OBJ | 7.1000 | 7.1000 | | |
| 1 | ∞ | 0.3500 | 1.88299 | 40.78 |
| 2 | 0.9530 | 0.3000 | | |
| 3 | ∞ | 0.3500 | 2.00100 | 29.13 |
| 4 | ∞ | 0.0350 | | |
| 5 | ∞ | 0.2500 | 2.00100 | 29.13 |
| 6 | 0.7780 | 0.6500 | 1.75520 | 27.51 |
| 7 | −1.4260 | 0.5000 | | |
| 8 (St) | ∞ | 0.0350 | | |
| 9 | ∞ | 0.6400 | 1.43875 | 94.66 |
| 10 | −1.0220 | 0.1000 | | |
| 11 | −41.3310 | 0.7300 | 1.43875 | 94.66 |
| 12 | −0.7030 | 0.2500 | 1.80518 | 25.42 |
| 13 | −1.2500 | 0.3967 | | |
| 14 | ∞ | 1.2500 | 1.55919 | 53.90 |
| 15 | ∞ | 1.1500 | 1.55919 | 53.90 |
| 16 | ∞ | 0.4000 | 1.47144 | 65.41 |
| 17 | ∞ | 0.0030 | | |

TABLE 10

Example 5

| | |
|---|---|
| f | 1.021 |
| Bf | 2.074 |
| FNo. | 7.80 |
| 2ω (°) | 134.4 |

Example 6

Figure 11:
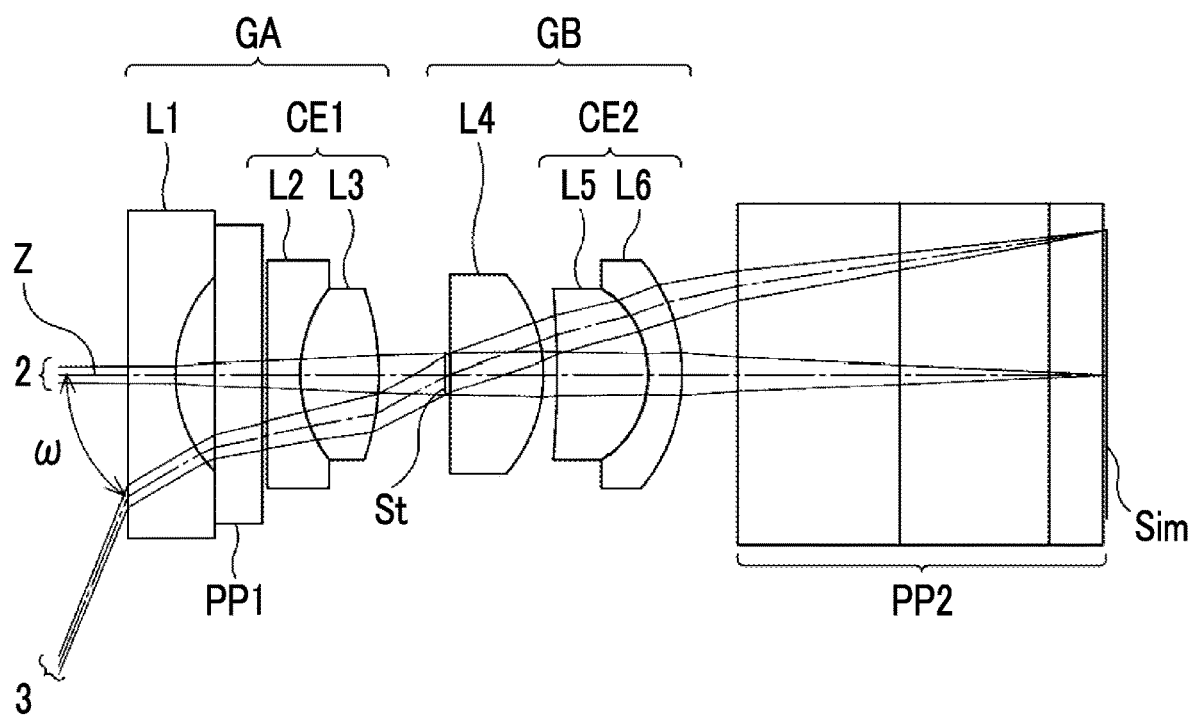
FIG. 11 is a cross-sectional view showing the configuration and optical paths of an objective optical system for an endoscope of Example 6.
Figure 12:
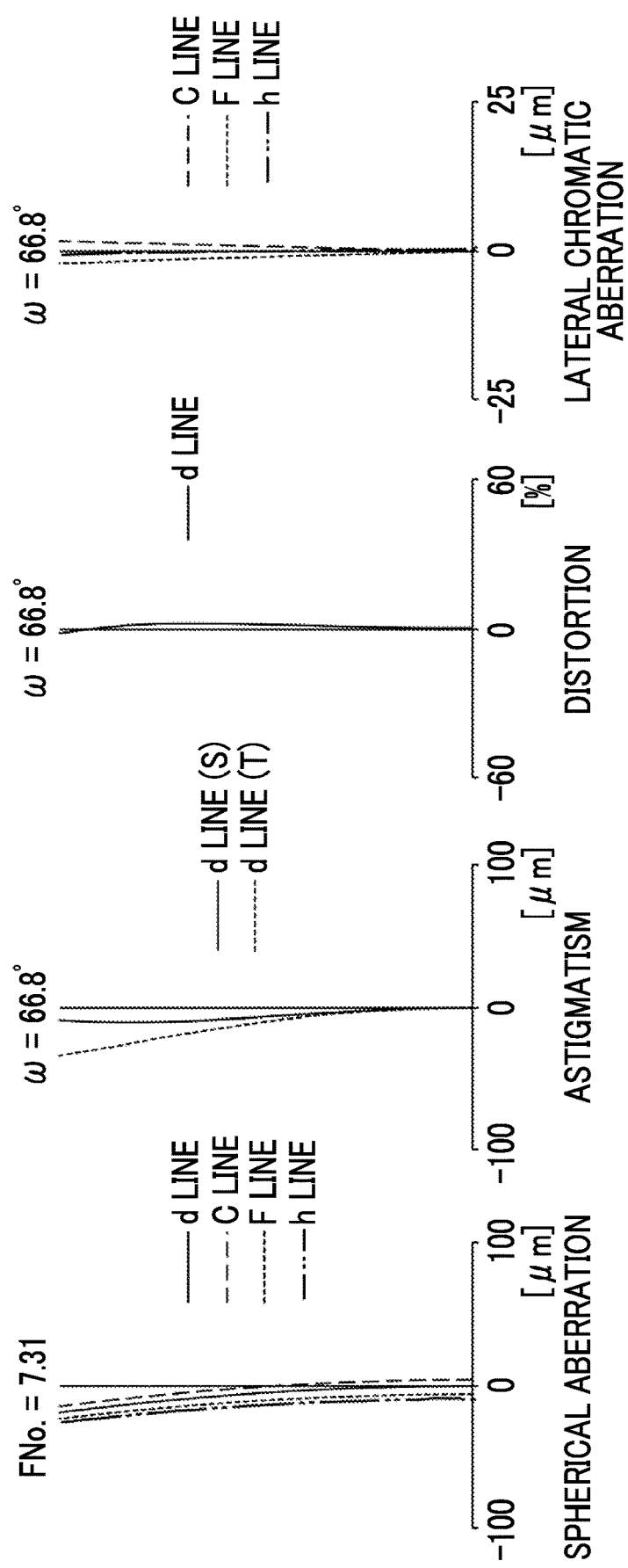
FIG. 12 is a diagram showing the respective aberrations of the objective optical system for an endoscope of Example 6.

A cross-sectional view showing the configuration and optical paths of an objective optical system for an endoscope of Example 6 is shown in FIG. 11, the basic lens data thereof are shown in Table 11, the specifications thereof are shown in Table 12, and a diagram showing the respective aberrations thereof is shown in FIG. 12.

TABLE 11

Example 6

| Sn | R | D | Nd | vd |
|---|---|---|---|---|
| OBJ | 7.1000 | 7.1000 | | |
| 1 | ∞ | 0.3500 | 1.88299 | 40.78 |
| 2 | 0.9530 | 0.2904 | | |
| 3 | ∞ | 0.3500 | 2.00100 | 29.13 |
| 4 | ∞ | 0.0350 | | |
| 5 | ∞ | 0.2500 | 2.00100 | 29.13 |
| 6 | 0.9530 | 0.5800 | 1.80518 | 25.42 |
| 7 | −1.7420 | 0.4900 | | |
| 8 (St) | ∞ | 0.0350 | | |
| 9 | ∞ | 0.6900 | 1.43875 | 94.66 |
| 10 | −1.0220 | 0.1000 | | |
| 11 | −6.5100 | 0.6700 | 1.59522 | 67.73 |
| 12 | −0.7030 | 0.2500 | 2.00100 | 29.13 |
| 13 | −1.2120 | 0.4116 | | |
| 14 | ∞ | 1.2000 | 1.55919 | 53.90 |
| 15 | ∞ | 1.1000 | 1.55919 | 53.90 |
| 16 | ∞ | 0.4000 | 1.47144 | 65.41 |
| 17 | ∞ | 0.0264 | | |

TABLE 12

Example 6

| | |
|---|---|
| f | 0.959 |
| Bf | 2.065 |
| FNo. | 7.31 |
| 2ω (°) | 133.6 |

Values of the objective optical systems for an endoscope of Examples 1 to 6 corresponding to Conditional expressions (1) to (7) are shown in Table 13. In Examples 1 to 6, a d line is used as a reference wavelength. Table 13 shows values with respect to a d line.

TABLE 13

| Expression number | Conditional expression | Example 1 | Example 2 | Example 3 | Example 4 | Example 5 | Example 6 |
|---|---|---|---|---|---|---|---|
| (1) | fA/fB | −1.838 | −1.957 | −1.710 | −1.721 | −1.654 | −1.662 |
| (2) | \|vd2 − vd3\| | 3.89 | 0.66 | 3.89 | 3.89 | 1.62 | 3.71 |
| (3) | {R23/(Nd3 − Nd2)}/f | −5.594 | −6.308 | −4.886 | −5.613 | −3.101 | −5.074 |

TABLE 13-continued

| Expression number | Conditional expression | Example 1 | Example 2 | Example 3 | Example 4 | Example 5 | Example 6 |
|---|---|---|---|---|---|---|---|
| (4) | {R56/(Nd6 − Nd5)}/f | −1.599 | −1.492 | −1.628 | −1.864 | −1.879 | −1.806 |
| (5) | f23/f56 | 0.583 | 0.590 | 0.679 | 0.663 | 0.583 | 0.829 |
| (6) | (R23 + R3r)/(R23 − R3r) | −0.293 | −0.332 | −0.372 | −0.293 | −0.294 | −0.293 |
| (7) | \|vd5 − vd6\| | 56.09 | 56.09 | 49.24 | 42.28 | 69.23 | 38.60 |

It is found from the above-mentioned data that the maximum total angle of view is a wide angle of view of 130° or more since each of the objective optical systems for an endoscope of Examples 1 to 6 satisfies Conditional expressions (1) to (7) and satisfactorily corrects various aberrations including a chromatic aberration in the entire range to a visible range from a short wavelength range near a wavelength of 400 nm (nanometer) with a small outer diameter of the lens.

Figure 13:
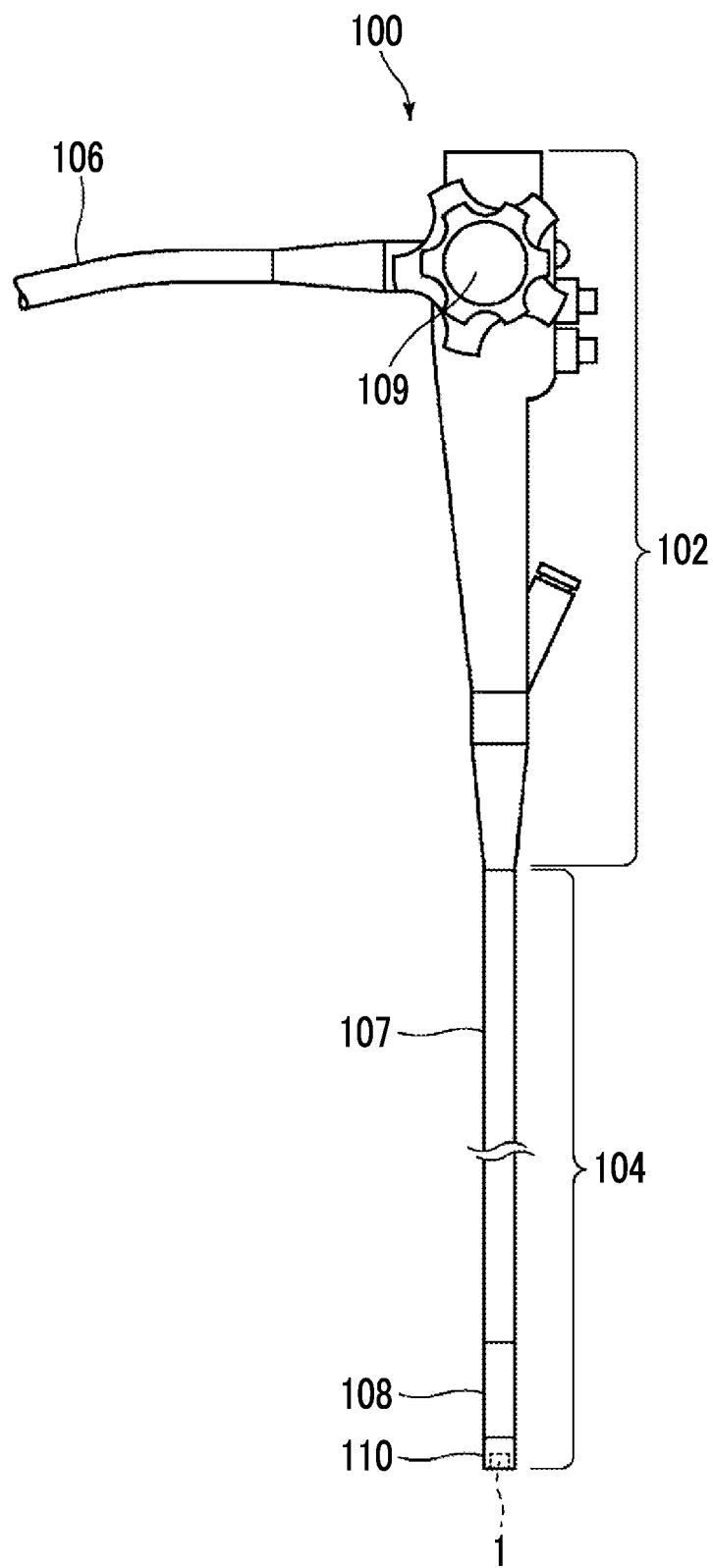
FIG. 13 is a diagram showing the schematic configuration of an endoscope according to an exemplary embodiment.

Next, an endoscope according to an exemplary embodiment of the present disclosure will be described. A diagram showing the entire schematic configuration of the endoscope according to the exemplary embodiment of the present disclosure is shown in FIG. 13. The endoscope 100 shown in FIG. 13 mainly comprises an operation part 102, an insertion part 104, and a universal cord 106 that is to be connected to a connector part (not shown). A large portion of the insertion part 104 is a soft portion 107 that is bendable in any direction along an insertion path, a bendable portion 108 is connected to the distal end of the soft portion 107, and a distal end portion 110 is connected to the distal end of the bendable portion 108. The bendable portion 108 is provided to allow the distal end portion 110 to face in a desired direction, and can be operated to be bent by the rotational movement of bending operation knobs 109 provided on the operation part 102. An objective optical system 1 for an endoscope according to the exemplary embodiment of the present disclosure is provided in the distal end of the distal end portion 110. The objective optical system 1 for an endoscope is schematically shown in FIG. 13.

Since the endoscope according to this exemplary embodiment comprises the objective optical system for an endoscope according to the exemplary embodiment of the present disclosure, the diameter of the insertion part 104 can be reduced and an observation can be made with a wide angle of view. Further, since the endoscope can acquire a good image over the entire range to a visible range from a short wavelength range near a wavelength of 400 nm (nanometer), the endoscope can be suitably applied to the observation of an image in which blood vessels, surface structures, or the like are enhanced and which is obtained from the combination of the use of white light and a laser beam having a wavelength of about 400 nm (nanometer) and image processing.

The present disclosure has been described above using the exemplary embodiments and Examples, but the present disclosure can have various modifications without being limited to the exemplary embodiments and Examples. For example, the curvature radius, the surface spacing, the refractive index, and the Abbe number of each lens may have other values without being limited to the values shown in the respective numerical examples.

The entire content of the present disclosure of Japanese Patent Application No. 2019-193768, filed Oct. 24, 2019, is incorporated in this specification by reference. All documents, patent applications, and technical standards disclosed in this specification are incorporated in this specification by reference so that the incorporation of each of the documents, the patent applications, and the technical standards by reference is specific and is as detailed as that in a case where the documents, the patent applications, and the technical standards are described individually.

What is claimed is:

1. An objective optical system for an endoscope consisting of, in order from an object side toward an image side: a front group having negative focal power; an aperture stop; and a rear group having positive focal power, wherein:
   the front group includes only three lenses, which consist of, in order from the object side toward the image side: a first lens having negative focal power; a second lens having negative focal power; and a third lens having positive focal power, as lenses,
   the rear group includes only three lenses, which consist of, in order from the object side toward the image side: a fourth lens having positive focal power; a fifth lens having positive focal power; and a sixth lens having negative focal power, as lenses,
   the second lens and the third lens are cemented to each other,
   the fifth lens and the sixth lens are cemented to each other, and
   in a case where
      a focal length of the objective optical system for an endoscope is denoted by f,
      a focal length of the front group is denoted by fA,
      a focal length of the rear group is denoted by fB,
      an Abbe number of the second lens with respect to a d line is denoted by vd2,
      an Abbe number of the third lens with respect to a d line is denoted by vd3,
      a refractive index of the second lens with respect to a d line is denoted by Nd2,
      a refractive index of the third lens with respect to a d line is denoted by Nd3, and
      a curvature radius of a cemented surface between the second lens and the third lens is denoted by R23,
   Conditional expressions (1), (2), and (3) are satisfied, which are represented by $$-5 < fA/fB < -1.4 \tag{1}$$

$$0 < |vd2 - vd3| < 10 \tag{2}$$

$$-6.8 < \{R23/(Nd3 - Nd2)\}/f < 0 \tag{3}$$

2. The objective optical system for an endoscope according to claim 1, wherein a lens surface of the first lens facing the object side is a flat surface.

3. The objective optical system for an endoscope according to claim 1, wherein:
   in a case where
      a refractive index of the fifth lens with respect to a d line is denoted by Nd5,
      a refractive index of the sixth lens with respect to a d line is denoted by Nd6, and a curvature radius of a cemented surface between the fifth lens and the sixth lens is denoted by R56, Conditional expression (4) is satisfied, which is represented by $$-2<\{R56/(Nd6-Nd5)\}/f<0 \qquad (4).$$

4. The objective optical system for an endoscope according to claim 1, wherein:

in a case where
a composite focal length of the second lens and the third lens is denoted by f23 and
a composite focal length of the fifth lens and the sixth lens is denoted by f56, Conditional expression (5) is satisfied, which is represented by $$0<f23/f56<1 \qquad (5).$$

5. The objective optical system for an endoscope according to claim 1, wherein:

in a case where a curvature radius of a lens surface of the third lens facing the image side is denoted by R3r, Conditional expression (6) is satisfied, which is represented by $$-0.45<(R23+R3r)/(R23-R3r)<-0.25 \qquad (6).$$

6. The objective optical system for an endoscope according to claim 1, wherein:

in a case where
an Abbe number of the fifth lens with respect to a d line is denoted by vd5 and
an Abbe number of the sixth lens with respect to a d line is denoted by vd6, Conditional expression (7) is satisfied, which is represented by $$35<|vd5-vd5|<75 \qquad (7).$$

7. The objective optical system for an endoscope according to claim 1, wherein Conditional expression (1-1) is satisfied, which is represented by $$-2.2<fA/fB<-1.6 \qquad (1-1).$$

8. The objective optical system for an endoscope according to claim 1, wherein Conditional expression (2-1) is satisfied, which is represented by $$0.5<|vd2-vd3|<5 \qquad (2-1).$$

9. The objective optical system for an endoscope according to claim 1, wherein Conditional expression (3-1) is satisfied, which is represented by $$-6.4<\{R23/(Nd3-Nd2)\}/f<-3 \qquad (3-1).$$

10. The objective optical system for an endoscope according to claim 3, wherein Conditional expression (4-1) is satisfied, which is represented by $$-1.9<\{R56/(Nd6-Nd5)\}/f<-1.4 \qquad (4-1).$$

11. The objective optical system for an endoscope according to claim 4, wherein Conditional expression (5-1) is satisfied, which is represented by $$0.56<f23/f56<0.83 \qquad (5-1).$$

12. The objective optical system for an endoscope according to claim 5, wherein Conditional expression (6-1) is satisfied, which is represented by $$0.4<(R23+R3r)/(R23-R3r)<-0.28 \qquad (6-1).$$

13. The objective optical system for an endoscope according to claim 6, wherein Conditional expression (7-1) is satisfied, which is represented by $$38<|vd5-vd6|<70 \qquad (7-1).$$

14. An endoscope comprising the objective optical system for an endoscope according to claim 1.

\* \* \* \* \*